United States Patent
Ronay et al.

(10) Patent No.: US 12,298,128 B2
(45) Date of Patent: May 13, 2025

(54) MULTI-AXIS DIFFERENTIAL STRAIN SENSOR

(71) Applicant: Liquid Wire Inc., Portland, OR (US)

(72) Inventors: Mark William Ronay, Portland, OR (US); Trevor Antonio Rivera, Portland, OR (US); Jorge E. Carbo, Jr., Portland, OR (US); Michael Adventure Hopkins, Portland, OR (US)

(73) Assignee: Liquid Wire Inc., Portland, OR (US)

( * ) Notice: Subject to any disclaimer, the term of this patent is extended or adjusted under 35 U.S.C. 154(b) by 248 days.

(21) Appl. No.: 18/001,443

(22) PCT Filed: Jun. 11, 2021

(86) PCT No.: PCT/US2021/070696
§ 371 (c)(1),
(2) Date: Dec. 9, 2022

(87) PCT Pub. No.: WO2021/253050
PCT Pub. Date: Dec. 16, 2021

(65) Prior Publication Data
US 2023/0221105 A1    Jul. 13, 2023

Related U.S. Application Data

(60) Provisional application No. 63/038,547, filed on Jun. 12, 2020.

(51) Int. Cl.
*G01B 7/16* (2006.01)

(52) U.S. Cl.
CPC ..................... *G01B 7/18* (2013.01)

(58) Field of Classification Search
CPC .................................................. G01B 7/18
See application file for complete search history.

(56) References Cited

U.S. PATENT DOCUMENTS

| 7,854,173 B2 | 12/2010 | Cheng et al. |
| 2018/0247727 A1 | 8/2018 | Ronay |

(Continued)

FOREIGN PATENT DOCUMENTS

| CN | 107300435 A | 10/2017 |
| EP | 3457103 A1 | 3/2019 |

(Continued)

OTHER PUBLICATIONS

"International Application Serial No. PCT/US2021/070696, International Search Report mailed Aug. 31, 2021", 5 pgs.

(Continued)

*Primary Examiner* — Eric S. McCall
(74) *Attorney, Agent, or Firm* — Quinn IP Law (57) ABSTRACT

A flexible differential strain sensor, system, and method includes a deformable substrate having a first axis and a second axis different than the first axis and a first sensing element and a second sensing element. The first and second sensing elements are comprised of conductive gel. The first sensing element is arranged to sense strain in the deformable substrate along the first axis. The second sensing element has a first portion arranged to sense strain in the deformable substrate along the first axis and a second portion arranged to sense strain in the deformable substrate along the second axis. The second sensing element is arranged to cancel at least a portion of the stimulus sensed by the first sensing element in the along the first axis.

20 Claims, 5 Drawing Sheets

(56) References Cited

U.S. PATENT DOCUMENTS

2020/0100859 A1  4/2020  Shen et al.
2024/0172963 A1* 5/2024  Carbo, Jr. ................ A61B 5/11

FOREIGN PATENT DOCUMENTS

| JP | 2020020816 A | 2/2020 |
| KR | 20180107375 A | 10/2018 |
| WO | WO-2015033669 A1 | 3/2015 |
| WO | WO-2019098049 A1 | 5/2019 |
| WO | WO-2021253050 A1 | 12/2021 |

OTHER PUBLICATIONS

"International Application Serial No. PCT/US2021/070696, Written Opinion mailed Aug. 31, 2021", 8 pgs.

* cited by examiner

MULTI-AXIS DIFFERENTIAL STRAIN SENSOR

CROSS-REFERENCE TO RELATED APPLICATIONS

This patent application is a U.S. National Stage Filing under 35 U.S.C. 371 from International Application No. PCT/US2021/070696, filed Jun. 11, 2021, which claims the benefit of priority to U.S. Provisional Application Ser. No. 63/038,547, filed Jun. 12, 2020, each of which are incorporated by reference herein in their entirety.

BACKGROUND

Strain sensors may measure a mechanical or otherwise physical stimulus on the strain sensor, e.g., by way of a substrate on which the strain sensor has been placed and thereby measure strain on the substrate. Deformation in the substrate translated to the strain sensor, such as stretching, twisting, flexing, and the like, may produce a change in some physical property of the strain sensor. The change in the physical property may be translated to strain and utilized to identify change in strain over time.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Flexible strain sensors have been disclosed, e.g., in U.S. Patent Application Publication No. 2018/0247727 ("the '727 application"), published on Aug. 30, 2018, which is incorporated by reference herein in its entirety. The '727 application discloses methods, apparatus, and example embodiments for strain sensing with deformable conductors, such as conductive gel, for example, in FIGS. 7-10 and in paragraphs [0014] through [0017] and [0089] through [0120], among others. As disclosed in the '727 application, sensor systems include sensor elements which respond to stimuli by changing dimensions, for example, stretching. Examples disclosed in the '727 application, for example, at paragraph [00116], may include variable resistor grid patterns and/or unconnected or sparsely connected variable resistor networks.

Disclosed herein are flexible differential strain sensors that can be used to measure, and differentiate between, stimuli that occur in two or more dimensions (e.g., along two different axes) by arranging sensor elements in patterns. Examples disclosed herein may utilize differential signal processing to provide for the strain along specific axes of a substrate. Consequently, such flexible differential strain sensors may provide relatively enhanced sensitivity to the nature of strain on a substrate and/or on the strain sensor.

Figure 1:
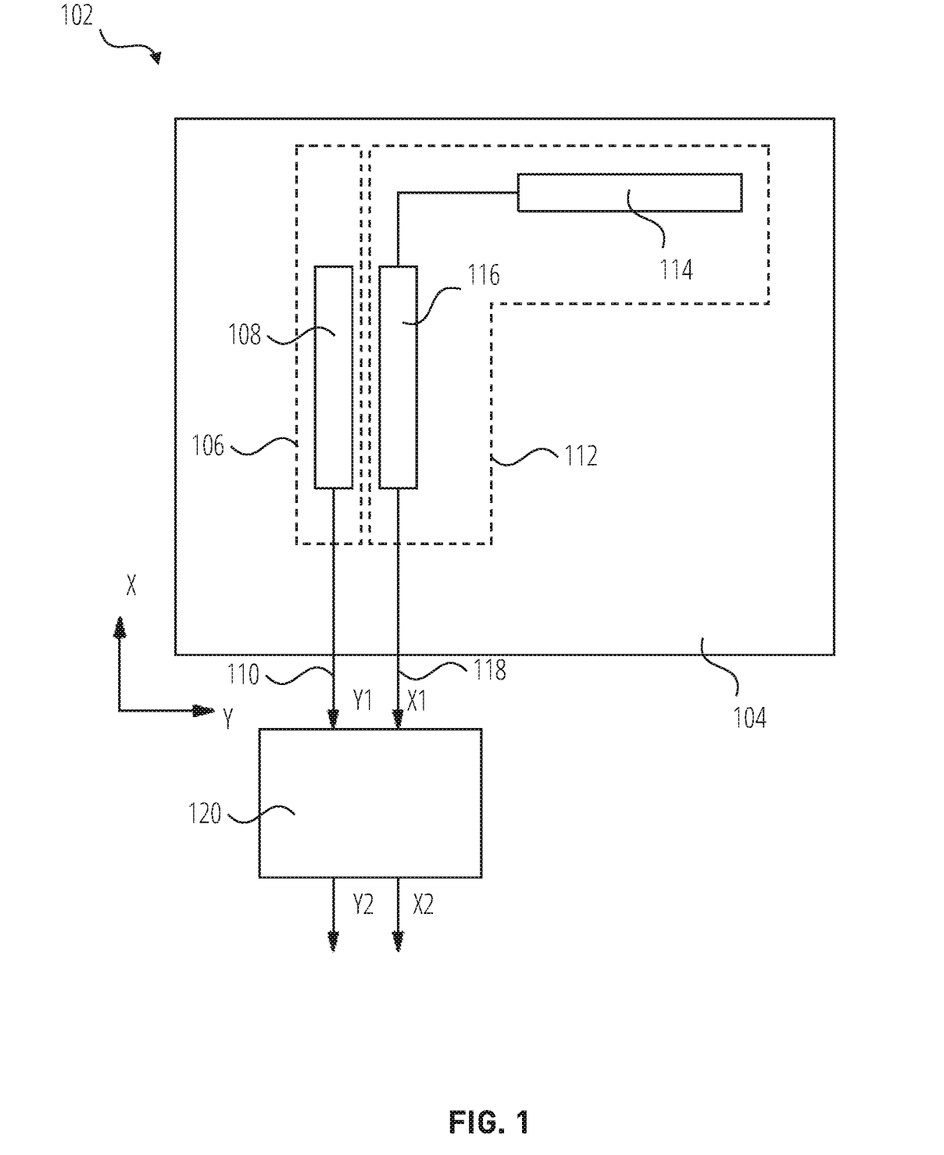
FIG. 1 is a block diagram of a flexible differential strain sensor, in an example embodiment.

FIG. 1 is a block diagram of a flexible differential strain sensor, in an example embodiment. The flexible differential strain sensor 102 is configured to detect strain on a deformable substrate 104 and, in particular, along the X and Y axes of the deformable substrate 104. The deformable substrate 104 may be any object onto or into which a conductive gel disclosed herein may be positioned and generally secured. The deformable substrate 104 may be or may include natural and synthetic fabrics, natural or synthetic rubbers, elastomers, and so forth. Further, in various alternative examples, the flexible differential strain sensor 102 may be implemented on a substrate that is intended to deform relatively little if at all but to allow the flexible differential strain sensor 102 to detect potentially undesirable strain or deformation on the substrate. For instance, the substrate may be metal, carbon fiber, or the like, and the flexible differential strain sensor 102 may generally be directed at identifying strain on such structures. However, in various examples, the flexible differential strain sensor 102 is implemented with the deformable substrate 104, in which case the flexible differential strain sensor 102 with the deformable substrate 104 may be placed on and secured to such relatively less deformable structures in order to determine the strain on such structures.

For the purposes of illustration, the deformable substrate 104 is presented effectively as a two-dimensional object with strain placed on one or both of the X and Y axes and detected by components which run directly along one of the X and Y axes. However, it is to be recognized and understood that components may be positioned at angles to the X and Y axes and that conventional mathematics may be utilized to compensate or otherwise account for the differences in angles relative to the X and Y axes. Moreover, strain may be placed on the deformable substrate 104 on a Z-axis orthogonal to the X and Y axes and that the flexible differential strain sensor 102 may be sensitive to such strain. Further, as will be illustrated herein, the principles illustrated in two-dimensional examples may be applied to three-dimensional examples, with strain sensors positioned along the Z-axis of the deformable substrate 104 and configured to directly sense strain placed on the Z-axis.

The flexible differential strain sensor 102 may include a first sensing element 106 having a first active portion 108 arranged to sense a strain along the Y-axis, e.g., a first axis. A first terminal 110 provides an electrical output from the first sensing element 106. A second sensing element 112 may have a second active portion 114 and a cancellation portion 116, with a second terminal 118 providing an electrical output from the second sensing element 112. The second active portion 114 may be positioned on the deformable substrate 104 to sense a strain along the X-axis, e.g., a second axis, and the cancellation portion 116 may be positioned on the deformable substrate 104 to logically or mathematically cancel a strain along the Y-axis detected by the first active portion 108 of the first sensing element 106. Consequently, the first sensing element 106 may be sensitive to strain on the Y-axis but have little or no sensitivity to strain on the X-axis. By contrast, the second sensing element 112 may be sensitive to strain placed on both the X-axis and the Y-axis. In some examples, by arranging the cancellation portion 116 in physical proximity of the first active portion 108, the cancellation portion 116 experiences the same or nearly the same strain as the first active portion 108 along the Y-axis.

In various examples, the first sensing element 106 and the second sensing element 112 are each formed of conductive gel, as disclosed herein. The conductive gel may be positioned on or within the deformable substrate 104 through any suitable process, including printing, dispersion into filaments and voids of the deformable substrate 104, and so forth. The conductive gel may be implemented as one or more electrical traces that are configured to conduct current along the traces. The electrical properties of the conductive gel may change as the conductive gel stretches, contracts, or otherwise deforms, e.g., as strain is placed on the deformable substrate 104 and, by extension, the conductive gel. In various examples, the impedance (or more narrowly the resistance) of a given trace of conductive gel may increase or decrease as the trace stretches, contracts, or otherwise deforms. Such change in the resistance of the trace may be consistent with the amount of strain placed on the deformable substrate 104 in proximity of the trace. Consequently, the first active portion 108, second active portion 114, and cancellation portion 116 may be understood to be particular portions of conductive gel of electrical traces that extend along a respective one of the X and Y axes of the deformable substrate 104. While the impedance and/or other electrical properties of the conductive gel may change as the conductive gel is deformed, the conductive gel may be significantly less brittle and likely to break and be significantly more resilient than conventional conductors used in electronics.

Two signals, Y1 on the first terminal 110 and X1 on the second terminal 118, may form an output vector from the flexible differential strain sensor 102 to recover and/or represent a strain field applied to the deformable substrate 104 and to the flexible differential strain sensor 102 generally. The output vector may be processed in any suitable manner. For example, in some applications, raw signals X1 and Y1 from may be processed by a signal processing unit 120 to determine and output strain placed the Y-axis as output signal Y2 and determine and output strain placed on the X-axis as output signal X2. The signal processing unit 120 may include an ohmmeter or other instrument for determining impedance at the terminals 110, 118 and a processor or other computational electronics that may convert or otherwise associate impedance or changes in impedance to strain on the flexible differential strain sensor 102. For instance, in an example implementation, a change of 0.03 Ohms in the impedance and/or resistance detected by the signal processing unit 120 is the equivalent to one (1) millimeter of strain on the conductive gel of the flexible differential strain sensor 102 and the trace formed thereby, as disclosed herein. In various examples, strain may be understood to be a change in overall length, though it is to be recognized and understood that any viable metric for strain known in the art may be utilized in addition or alternatively.

Because Y1 has a significant sensitivity to strain in the Y-axis by virtue of having the first active portion 108 but not having an trace that extends generally along the X-axis, as the second active portion 114 does, the signal processing unit 120 may compute the strain on the Y-axis by relating the change in impedance of the first active portion 108 to the strain on the Y-axis and outputting the resultant strain as Y2. In various examples, the signal processing unit 120 may simply buffer or pass through the signal Y1 as the output signal Y2 to provide an indication of the strain and a remote processing unit, controller, or other electronic equipment may perform the operations to relate change in impedance to strain on the flexible differential strain sensor 102.

By contrast, because the second sensing element 112 includes significant sensitivity to strain on both the X-axis and the Y-axis, the signal processing unit 120 may generate an output signal X2 that is indicative of strain placed along the X axis of the second sensing element 112 by subtracting the change in impedance from Y1 from the change in impedance from X1. Consequently, the signal processing unit 120 determines a differential sensitivity to impedance that substantially cancels out the strain placed the first active portion 108 and the cancellation portion 116 along the Y-axis and leaving X2 primarily or entirely based on the change in impedance along the second active portion 114. It is to be recognized and understood that for the purposes of this disclosure that while the first active portion 108 and cancellation portion 116 may be placed in close proximity of one another and formed of conductive gel traces that of very similar properties, variations in the actual positioning of the conductive gel may result in some margin of error between the change in impedance in the first active portion 108 and the cancellation portion 116, which may propagate through the differential calculation of the strain on the X-axis output at X2. However, it is to be recognized and understood that such small margins of error may nonetheless produce useful and accurate representations of strain on the X-axis even if the output X2 does not completely exclude the influence of strain on the Y-axis. The same principles apply to the output of Y2.

As noted above, any processing of the output vector may be implemented in a manner that may be customized to a specific application. In general, sensing elements may be arranged in grids or arrays that may be partially and/or fully connected. The elements may generate an output vector of values that may be analyzed to provide a representation of a strain field on the deformable substrate 104 measured by the flexible differential strain sensor 102, either alone or in combination with other sensors. The interpretation of the strain field may be based on the application, some examples of which are described below.

In other embodiments, the flexible differential strain sensor 102 may be arranged in other configurations and using different numbers and/or types of sensing elements, active and/or canceling regions, etc. For examples, sensing elements may be arranged in a T-shape, a U-shape, an S-shape, a box shape, etc. The different elements and/or regions may be arranged at other than right angles such as acute and/or obtuse angles. Sensing elements may be incorporated into any arbitrary patterns, and the signal processing may be adjusted to accommodate the different patterns. In some embodiments, signal processing may extract composite signals indicative of stimulus in one dimension while canceling strain in one or more other dimensions and/or axes. These principles may be applied to flexible differential strain sensors 102 with any number of elements, each element having any number of portions, both active and/or canceling, for any type of stimulus such as motion, stress, strain, etc.

Figure 2:
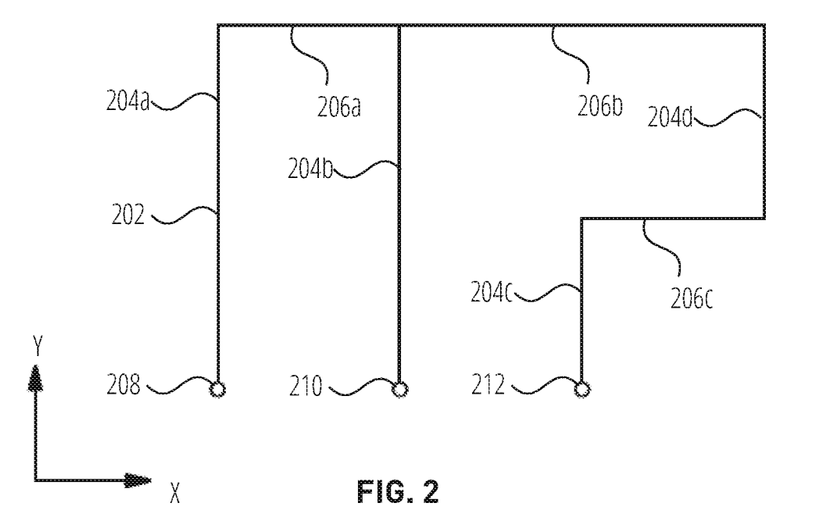
FIG. 2 is a topology of a flexible differential strain sensor, in an example embodiment.

FIG. 2 is a topology of the flexible differential strain sensor 102, in an example embodiment. In particular, the topology shows a conductive gel electrical trace 202. The trace 202 may be generally positioned as illustrated on the deformable substrate 104 (not shown) in order to produce the flexible differential strain sensor 102 illustrated in FIG. 1. The trace 202 includes Y-axis portions 204a, 204b, 204c, 204d, which may be understood to be portions of the trace 202 that extend generally along the Y-axis, and X-axis portions 206a, 206b, 206c that extend generally along the X-axis. The topology is not necessarily representative of relative lengths of the Y-axis portions 204a, 204b, 204c, 204d and the X-axis portions 206a, 206b, 206c.

The trace 202 is coupled to or otherwise forms a first node 208, a second node 210, and a third node 212. The first node 208 and the second node 210 generally describe the Y1 signal defined by the portions 204a, 206a, 204b. The second node 210 and the third node 212 generally describe the X1 signal and are defined by the portions 204b, 206b, 204d, 206c, and 204c. Thus, it is to be recognized that in terms of the actual topology, the signals X1 and Y1 are both influenced at least in part by the Y-axis portion 204b of the trace 202, and that a change in impedance along the Y-axis portion 204b may result in a change in impedance to both X1 and Y1.

Figure 3:
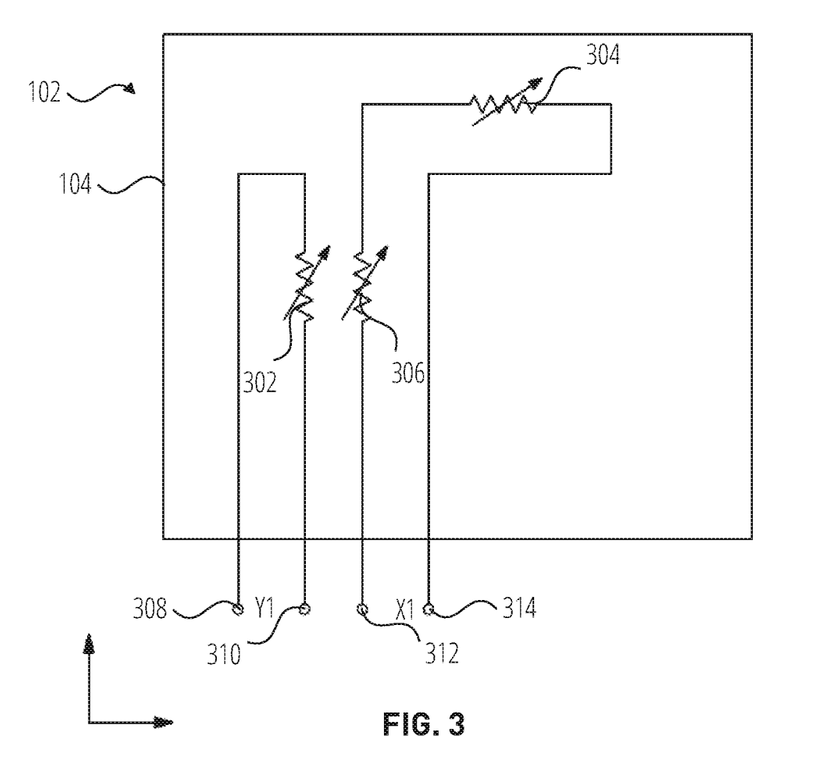
FIG. 3 is an electrical equivalent schematic of a flexible differential strain sensor, in an example embodiment.

FIG. 3 is an electrical equivalent schematic of the flexible differential strain sensor 102, in an example embodiment. The electrical equivalent schematic includes a first varistor 302 which corresponds to the first active portion 108, a second varistor 304 which corresponds to the second active portion 114, and a third varistor 306 which corresponds to the cancellation portion 116, all positioned on the deformable substrate 104. The electrical equivalent schematic further includes first logical node 308 and second logical node 310, across which signal Y1 is produced, and third logical node 312 and fourth logical node 314, across which signal X1 is produced. While varistors are discussed herein, it is to be recognized and understood that the varistors provide for the variable impedance produced by the deformation of the trace 202 generally rather than only resistance narrowly.

It is noted and emphasized that the electrical equivalent schematic of FIG. 3 is the product of the topology of FIG. 2. Thus, the first varistor 302 accounts for the variable impedance produced by the deformation of the trace 202 along the Y-axis portion 204a, X-axis portion 206a, and Y-axis portion 204b. In examples where the X-axis portion 206a is very short, e.g., one hundred micrometers or less, while the Y-axis portion 204a and the Y-axis portion 204b are each multiple millimeters or centimeters long, the first varistor 302 may represent the change in impedance and, by association, the strain placed along the Y-axis corresponding to those portions of the trace 202. Similarly, the second varistor 304 may correspond to the X-axis portion 206b and X-axis portion 206c while the third varistor 306 may correspond to the Y-axis portion 204b, Y-axis portion 204c, and Y-axis portion 204d. Further, the first logical node 308 may correspond to the first node 208, the second logical node 310 and the third logical node 312 may correspond to the second node 210, and the fourth logical node 314 may correspond to the third node 212.

However, it is to be recognized and understood that the principles of the electrical equivalent schematic may be obtained by any suitable arrangement of electrical components and is not tied to any particular topology nor to any particular electrical components. Thus, various examples of the flexible differential strain sensor 102 are not necessarily implemented with conductive gel to the extent that alternative components may be utilized which vary impedance as a function of localized strain on the deformable substrate 104 and/or on the components themselves. Similarly, the flexible differential strain sensor 102 as shown in FIG. 1 may be implemented without respect to variable impedance to the extent that alternative mechanisms are viable. However, implementations of the flexible differential strain sensor 102 with conductive gel may provide advantages of electrical and mechanical simplicity, robustness, resilience, and cost, among other factors, in comparison with potential alternative components. Such advantages may be seen both in use of the flexible differential strain sensor 102 as well as in the process of manufacturing the flexible differential strain sensor 102.

Figure 4A:
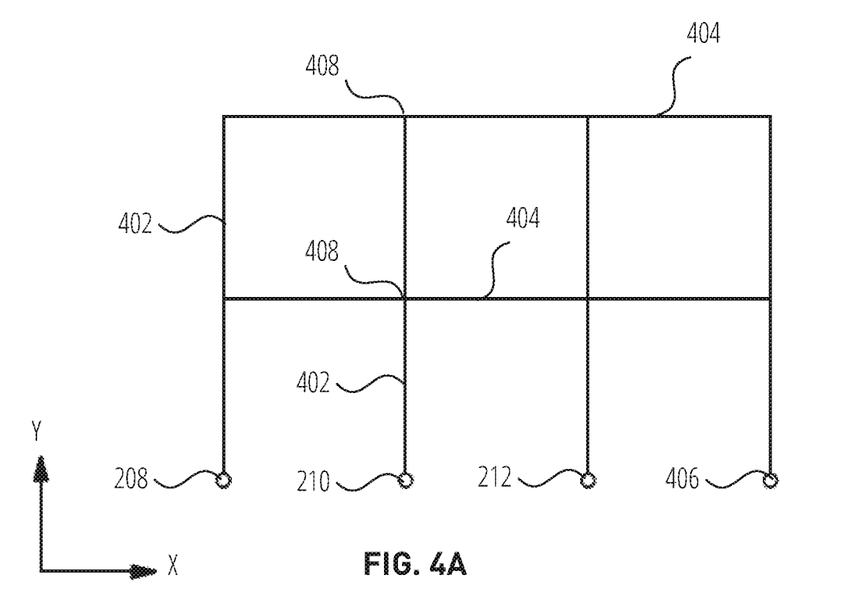
FIGS. 4A and 4B illustrate an abstract representation of a process by which a topology of a flexible differential strain sensor may be formed, in an example embodiment.
Figure 4B:
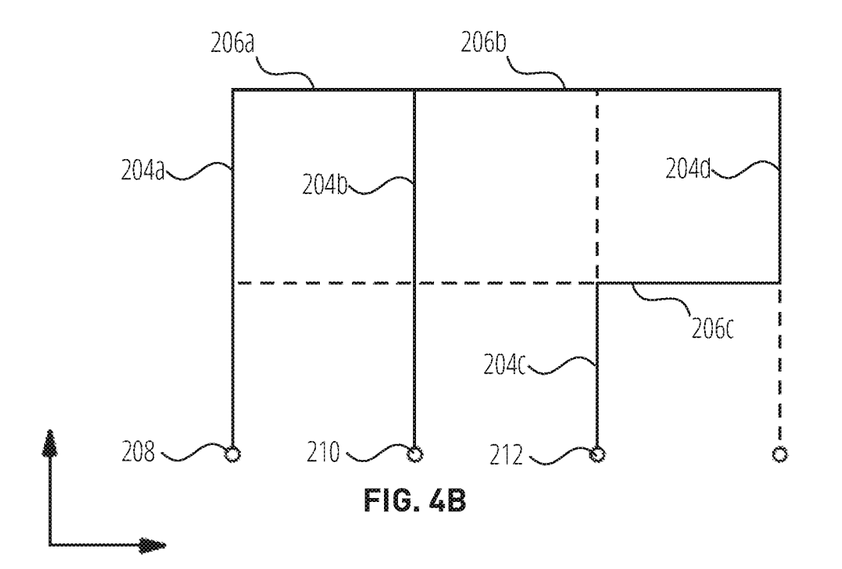

FIGS. 4A and 4B illustrate an abstract representation of a process by which the topology of FIG. 2 of the flexible differential strain sensor 102 may be formed, in an example embodiment. In FIG. 4A a grid of conductive gel is formed, including portions 402 aligned with the Y-axis, portions 404 aligned with the X-axis, along with the nodes 208, 210, 212 and a fourth node 406. In FIG. 4B certain portions 402, 404 of the grid are removed, as represented with dashed lines, e.g., by being cut or otherwise disconnected from the remainder of the conductive gel trace 202. The portions that remain, i.e., the solid lines, correspond to the trace 202 and various portions 204, 206 thereof, illustrated in the topology FIG. 2. Consequently, the fourth node 406 is also removed and not operative. While the grid structure of FIG. 4A is provided by way of example, it is to be recognized and understood that the grid may be enlarged or shrunk, with more or fewer portions 402, 404 and more or fewer nodes.

The formation of the initial grid in FIG. 4A may carry certain advantages over a process that simply produces the topology of FIG. 2 directly. In particular, the grid structure of FIG. 4A allows for an initial configuration that may readily be adapted to any final desired topology by removing unneeded portions. Moreover, the initial grid may be implemented as an unconnected/sparsely connected grid pattern, in which while some vertices are ultimately associated with an output node 208, 210, 212, 406, other vertices 408 are not ultimately associated with an output node 208, 210, 212, 406.

While the initial grid of FIG. 4A is included as part of a process by which the topology of FIG. 2 may be made, and that doing so may provide for certain advantages in adaptability of the manufacturing process to various use cases, it is emphasized that the topology of FIG. 2 may be arrived at directly without utilizing the initial grid. In such a case, the conductive gel may be applied in the topology without necessarily removing any portion of the conductive trace. While doing so may be less adaptable to different desired topologies, such a process may also be relatively faster to perform and result in less waste of conductive gel and other components.

Figure 5:
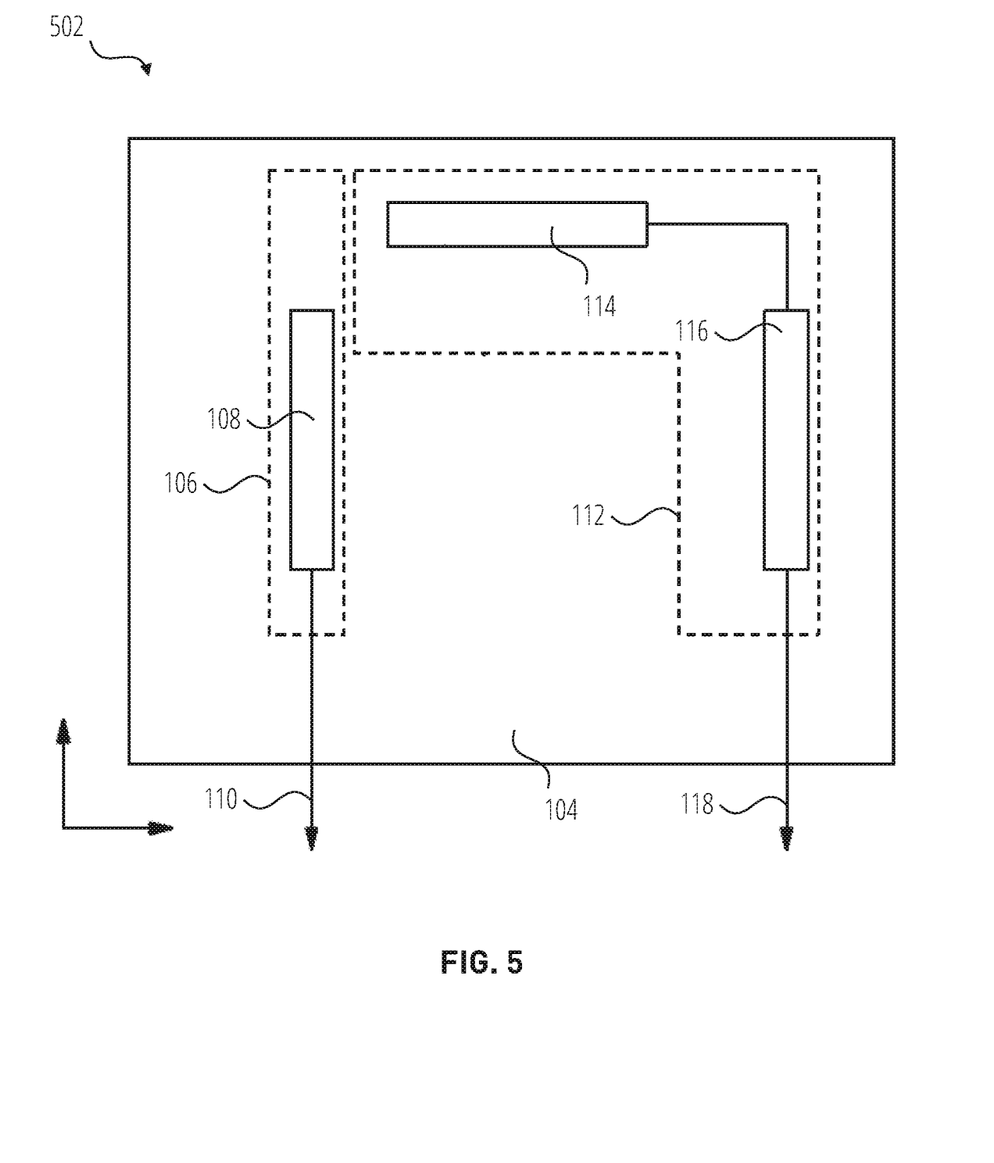
FIG. 5 is a block diagram of a flexible differential strain sensor, in an example embodiment.

FIG. 5 is a block diagram of a flexible differential strain sensor 502, in an example embodiment. The flexible differential strain sensor 502 includes many of the same components as the flexible differential strain sensor 102. Thus, the 502 may include the first sensing element 106 having the first active portion 108 arranged to sense a strain along the Y-axis. The first terminal 110 provides an electrical output from the first sensing element 106. The second sensing element 112 may have the second active portion 114 and the cancellation portion 116, with the second terminal 118 providing an electrical output from the second sensing element 112. The second active portion 114 may be positioned on the deformable substrate 104 to sense a strain along the X-axis and the cancellation portion 116 may be positioned on the deformable substrate 104 to logically or mathematically cancel a strain along the Y-axis detected by the first active portion 108 of the first sensing element 106. Consequently, the first sensing element 106 may be sensitive to strain on the Y-axis but have little or no sensitivity to strain on the X-axis. By contrast, the second sensing element 112 may be sensitive to strain placed on both the X-axis and the Y-axis. While a signal processing unit 120 is not illustrated it is to be recognized and understood that such a component may be included as part of the flexible differential strain sensor 502 as in the flexible differential strain sensor 102.

However, in contrast to the flexible differential strain sensor 102, the flexible differential strain sensor 502 generally forms a U-shape. As a result, the first active portion 108 is spaced apart from the cancellation portion 116. Consequently, the flexible differential strain sensor 502 may be relatively more sensitive to differential strain across a width of the deformable substrate 104 along the X-axis than the flexible differential strain sensor 102, but relatively less sensitive to differential strain proximate the first sensing element 106. It is to be recognized and understood that the principles discussed in relation to the relative differences between the flexible differential strain sensor 102 and the flexible differential strain sensor 502 may be applied to any of a variety of alternative flexible differential strain sensors, and that as a result various configurations may be implemented as desired.

Figure 6:
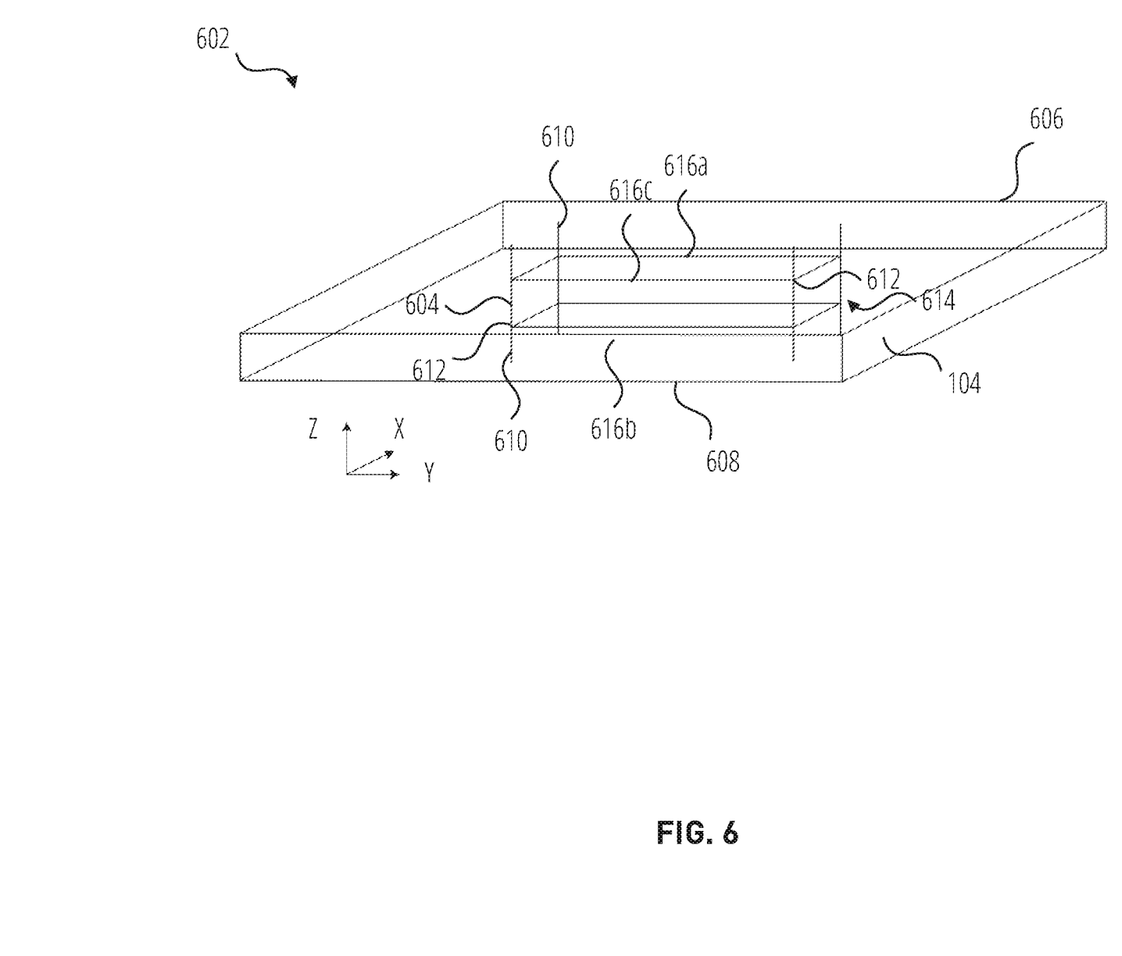
FIG. 6 is a topology of a three-dimensional flexible differential strain sensor, in an example embodiment.

FIG. 6 is a topology of a three-dimensional flexible differential strain sensor 602, in an example embodiment. The three-dimensional flexible differential strain sensor 602 is positioned on and within the deformable substrate 104 in all three axes X, Y, and Z. Consequently, in the illustrated example, the conductive gel trace 604 includes portions positioned on a top major surface 606, a bottom major surface 608, and through the deformable substrate 104 between the top major surface 606 and bottom major surface 608. As illustrated, the trace 604 further includes nodes 610 at the vertices 612, though as disclosed herein not all vertices 612 are nodes 610 but rather are utilized as nodes 610 as desired.

The topology is provided for the purposes of illustration and it is to be recognized and understood that the lengths may be exaggerated and are not necessary proportional. Thus, for instance, where the deformable substrate 104 is a textile used, for instance, in a shirt, the lengths of the portions of the trace 604 along the X and Y axes may be multiple millimeters or centimeters while the lengths of the trace 604 along the Z-axis may be a fraction of a millimeter, e.g., one hundred (100) micrometers or less. Other examples of various lengths are contemplated dependent on the circumstances in which the three-dimensional flexible differential strain sensor 602 is utilized.

Moreover, the topology is provided in a simplified format for the purposes of clarity but it is to be recognized and understood that an expanded three-dimensional grid pattern analogous to the grid pattern described with respect to FIGS. 4A and 4B may be utilized to increase the portions of the trace 604 and nodes 610 available. As with FIGS. 4A and 4B, the expanded grid pattern may allow for relatively more adaptability for the manufacturing process of the three-dimensional flexible differential strain sensor 602 and/or may allow for three-dimensional topologies other than the cube illustrated in FIG. 6. Additional three-dimensional topologies may be implemented without the intermediate step of the expanded three-dimensional grid as well.

The portions of the trace 604 that extend along the Z-axis may be understood to form a third sensing element 614 including at least one active portion and at least one cancellation portion, e.g., a third active portion and a second cancellation portion, based on the nomenclature presented with respect to the flexible differential strain sensor 102. Given that the illustrated topology of the three-dimensional flexible differential strain sensor 602 includes multiple portions of the trace 604 along each axis, the identification of each particular portion as an active portion or a cancellation portion may be subjective and subject to change at any given time dependent on the location on the deformable substrate 104 that is being assessed for strain. Consequently, a signal processing unit 120 may utilize any particular portion of the trace 604 as an active or cancellation portion as desired.

As with the wo dimensional flexible differential strain sensors 102, 502, the nodes 610 may be coupled to a signal processing unit 120 and variance in the impedance across various pairs of nodes 610 utilized as vectors to identify strain in three dimensions placed on the deformable substrate 104 and the three-dimensional flexible differential strain sensor 602 generally. In such an example, the resultant vector may include at least X1, Y1, and Z1, and may include more measurements along some or all of the axes based on which nodes 610 are utilized to form the vector. Further, the signal processing unit 120 may utilize parallel portions of the trace 604 to cancel out strain along the parallel axis. Thus, to cancel out strain along the Y-axis the signal processing unit 120 may, e.g., subtract the impedance between two nodes 610 that include the Y-axis portion 616*a* from the impedance between two nodes 610 that include the Y-axis portion 616*b*, or by subtracting the impedance between two nodes 610 that include the Y-axis portion 616*c* from the impedance between two nodes 610 that include the Y-axis portion 616*a*, among the various possible permutations.

In some embodiments, the flexible differential strain sensor 102, 502, 602 may be implemented as a flexible and/or stretchable strain sensor using one or more deformable conductors for the sensing elements such as the deformable substrates and/or conductors disclosed in the '727 application. In some embodiments, the strain sensors 102, 502, 602 may be fabricated using any of the materials and/or fabrication techniques described in U.S. Patent Application Publication No. 2020/0066628 published on Feb. 27, 2020 which is incorporated by reference herein in its entirety.

The strain sensors 102, 502, 602 may be employed in a wide variety of applications using myriad combinations of materials according to the principles of this disclosure. For example, a flexible and/or stretchable strain sensors 102, 502, 602 may be applied to and/or integrated with articles of clothing, shoes, hats, backpacks or other bags, industrial textiles, upholstery, geotextiles, non-textile membranes or any other article of manufacture in which strain sensing may be useful.

In some example embodiments, a strain sensors 102, 502, 602 fabricated with flexible and/or stretchable layers (e.g., various thermoset films, sheets, etc., and/or thermoplastic polyurethane (TPU)) may be integrated into an article of clothing such as a shirt or vest to sense the breathing of a person wearing the article. The sensor may be arranged such that the horizontal (X-axis) portion of the sensor or gauge is on the rib cage and parallel with the horizon if the wearer is standing. The vertical (Y-axis) portion of the sensor may be aligned with the wearer's spine, i.e., perpendicular to the horizon if the wearer is standing. In such a configuration, the output from both the X-axis and Y-axis portions of the strain sensors 102, 502, 602 may provide a response to breathing by the wearer, in various circumstances if the vertical (Y-axis) portion may respond to bending of the wearer's back.

As disclosed herein, some of the inventive principles of this disclosure relate to strain sensors 102, 502, 602 that may be sensitive to stimuli in two or more dimensions (e.g., along two different axes) in a manner that may differentiate between stimuli in different dimensions. For example, a sensor may include two sensing elements, each of which may have an active portion arranged to sense a stimulus along a different axis. One or both of the sensing elements may also have a cancelation portion that may be arranged to cancel the effects of a stimulus along the axis of the other sensing element. Such an arrangement may be useful, for example, to cancel unwanted artifacts of a stimulus in a different direction than that sought to be measured.

Such multi-axis strain sensors 102, 502, 602 can be used to differentiate between inputs in complex systems such as the human body. For example, such multi-axis sensor systems can be used to differentiate between gross motor movement, breathing, and changes in muscle dimensions caused by muscle flexing. Further by way of example, a strain sensor 102, 502, 602 system could include a sensing element affixed to apparel that stretches with rib cage expansion may use rib cage expansion to measure breathing. However, other movement, such as the bending of the torso, may also cause the sensor to stretch, leading to a potential inaccuracy in breathing measurement. However, if the strain sensor 102, 502, 602 included one sensing element arranged such that its axis extended perpendicularly to the spine and around a portion of the rib cage, and a second second sensing element arranged so that its axis extended in parallel with the spine, the sensing system could detect bending of the torso through deformation of the second sensing element, and could use information generated by the deformation of the second sensing element to differentiate between bending of the torso and breathing. Data generated by the strain sensor 102, 502, 602 could determine what portion of the stretching of the first sensor was not attributable to breathing, thus ensuring that the breathing measurements are more accurate.

As a further example, a multi-axis strain sensors 102, 502, 602 can be used to distinguish between the recruitment of different muscles in a given gross motor movement, or between different directional movements of a mechanical system. Another example application for strain sensors 102, 502, 602 according to this disclosure is in geotextiles for reinforcing beans, levies, or other earthwork structures where a multi-axis sensor may differentiate between normal settling and abnormal slumping or shifting which may indicate an impending collapse. Other example applications for multi-axis strain sensors 102, 502, 602 according to this disclosure include sails, e.g., for sailboats, windsurfers, etc., kites, parachutes, and/or the like. Additional examples include covering/cladding for machines such as articulating joints, shape memory alloy actuators, etc. Yet more examples include inflatable structures such as inflatable struts, tires, balloons, rafts, etc. Further examples include any structure such as a chassis, frame, housing, etc., that may warp, bend or otherwise deform in a manner that may be beneficial to sense and/or measure.

The embodiments and example implementation details described herein are for purposes of illustration. The drawings are not necessarily shown to scale. The inventive principles are not limited to these embodiments or details. The multiple inventive principles of this patent disclosure may have individual utility and benefits. When combined, however, the inventive principles described in this disclosure, including the portions incorporated by reference, may enable the individual elements to interact in novel ways to provide synergistic results.

The electrically conductive compositions, such as conductive gels, comprised in the articles described herein can, for example, have a paste like or gel consistency that can be created by taking advantage of, among other things, the structure that gallium oxide can impart on the compositions when gallium oxide is mixed into a eutectic gallium alloy. When mixed into a eutectic gallium alloy, gallium oxide can form micro or nano-structures that are further described herein, which structures are capable of altering the bulk material properties of the eutectic gallium alloy.

As used herein, the term "eutectic" generally refers to a mixture of two or more phases of a composition that has the lowest melting point, and where the phases simultaneously crystallize from molten solution at this temperature. The ratio of phases to obtain a eutectic is identified by the eutectic point on a phase diagram. One of the features of eutectic alloys is their sharp melting point.

The electrically conductive compositions can be characterized as conducting shear thinning gel compositions. The electrically conductive compositions described herein can also be characterized as compositions having the properties of a Bingham plastic. For example, the electrically conductive compositions can be viscoplastics, such that they are rigid and capable of forming and maintaining three-dimensional features characterized by height and width at low stresses but flow as viscous fluids at high stress. Thus, for example, the electrically conductive compositions can have a viscosity ranging from about 10,000,000 cP to about 40,000,000 cP under low shear and about 150 to 180 at high shear. For example under condition of low shear the composition has a viscosity of about 10,000,000 cP, about 15,000,000 cP, about 20,000,000 cP, about 25,000,000 cP, about 30,000,000 cP, about 45,000,000 cP, or about 40,000,000 cP under conditions of low shear. Under condition of high shear the composition has a viscosity of about 150 cP, about 155 cP, about 160 cP, 165 cP, about 170 cP, about 175 cP, or about 180 cP.

The electrically conductive compositions described herein can have any suitable conductivity, such as a conductivity of from about $2 \times 10^5$ S/m to about $8 \times 10^5$ S/m.

The electrically conductive compositions described herein can have any suitable melting point, such as a melting point of from about −20° C. to about 10° C., about −10° C. to about 5° C., about −5° C. to about 5° C. or about −5° C. to about 0° C.

The electrically conductive compositions can comprise a mixture of a eutectic gallium alloy and gallium oxide, wherein the mixture of eutectic gallium alloy and gallium oxide has a weight percentage (wt %) of between about 59.9% and about 99.9% eutectic gallium alloy, such as between about 67% and about 90%, and a wt % of between about 0.1% and about 2.0% gallium oxide such as between about 0.2 and about 1%, For example, the electrically conductive compositions can have about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater, such as about 99.9% eutectic gallium alloy, and about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, and about 2.0% gallium oxide.

The eutectic gallium alloy can include gallium-indium or gallium-indium-tin in any ratio of elements. For example, a eutectic gallium alloy includes gallium and indium. The electrically conductive compositions can have any suitable percentage of gallium by weight in the gallium-indium alloy that is between about 40% and about 95%, such as about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

The electrically conductive compositions can have a percentage of indium by weight in the gallium-indium alloy that is between about 5% and about 60%, such as about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%.

The eutectic gallium alloy can include gallium and tin. For example, the electrically conductive compositions can have a percentage of tin by weight in the alloy that is between about 0.001% and about 50%, such as about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

The electrically conductive compositions can comprise one or more micro-particles or sub-micron scale particles blended with the eutectic gallium alloy and gallium oxide. The particles can be suspended, either coated in eutectic gallium alloy or gallium and encapsulated in gallium oxide or not coated in the previous manner, within eutectic gallium alloy. The micro- or sub-micron scale particles can range in size from nanometer to micrometer and can be suspended in gallium, gallium-indium alloy, or gallium-indium-tin alloy. Particle to alloy ratio can vary and can change the flow properties of the electrically conductive compositions. The micro and nano-structures can be blended within the electrically conductive compositions through sonication or other suitable means. The electrically, conductive compositions can include a colloidal suspension of micro and nano-structures within the eutectic gallium alloy/gallium oxide mixture.

The electrically conductive compositions can further include one or more micro-particles or sub-micron scale particles dispersed within the compositions. This can be achieved in any suitable way, including by suspending particles, either coated in eutectic gallium alloy or gallium and encapsulated in gallium oxide or not coated in the previous manner, within the electrically conductive compositions or, specifically, within the eutectic gallium alloy fluid. These particles can range in size from nanometer to micrometer and can be suspended in gallium, gallium-indium alloy, or gallium-indium-tin alloy. Particle to alloy ratio can vary, in order to, among other things, change fluid properties of at least one of the alloy and the electrically conductive compositions. In addition, the addition of any ancillary material to colloidal suspension or eutectic gallium alloy in order to, among other things, enhance or modify its physical, electrical or thermal properties. The distribution of micro and nano-structures within the at least one of the eutectic gallium alloy and the electrically conductive compositions can be achieved through any suitable means, including sonication or other mechanical means without the addition of particles. In certain embodiments, the one or more micro-particles or sub-micron particles are blended with the at least one of the eutectic gallium alloy and the electrically conductive compositions with wt % of between about 0.001% and about 40.0% of micro-particles, for example about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40.

The one or more micro- or sub-micron particles can be made of any suitable material including soda glass, silica, borosilicate glass, quartz, oxidized copper, silver coated copper, non-oxidized copper, tungsten, super saturated tin granules, glass, graphite, silver coated copper, such as silver coated copper spheres, and silver coated copper flakes, copper flakes, or copper spheres, or a combination thereof, or any other material that can be wetted by the at least one of the eutectic gallium alloy and the electrically conductive compositions. The one or more micro-particles or sub-micron scale particles can have any suitable shape, including the shape of spheroids, rods, tubes, a flakes, plates, cubes, prismatic, pyramidal, cages, and dendrimers. The one or more micro-particles or sub-micron scale particles can have any suitable size, including a size range of about 0.5 microns to about 60 microns, as about 0.5 microns, about 0.6 microns, about 0.7 microns, about 0.8 microns, about 0.9 microns, about 1 microns, about 1.5 microns, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, about 25 microns, about 26 microns, about 27 microns, about 28 microns, about 29 microns, about 30 microns, about 31 microns, about 32 microns, about 33 microns, about 34 microns, about 35 microns, about 36 microns, about 37 microns, about 38 microns, about 39 microns, about 40 microns, about 41 microns, about 42 microns, about 43 microns, about 44 microns, about 45 microns, about 46 microns, about 47 microns, about 48 microns, about 49 microns, about 50 microns, about 51 microns, about 52 microns, about 53 microns, about 54 microns, about 55 microns, about 56 microns, about 57 microns, about 58 microns, about 59 microns, or about 60 microns.

The electrically conductive compositions described herein can be made by any suitable method, including a method comprising blending surface oxides formed on a surface of a eutectic gallium alloy into the bulk of the eutectic gallium alloy by shear mixing of the surface oxide/alloy interface. Shear mixing of such compositions can induce a cross linked microstructure in the surface oxides; thereby forming a conducting shear thinning gel composition. A colloidal suspension of micro-structures can be formed within the eutectic gallium alloy/gallium oxide mixture, for example as, gallium oxide particles and/or sheets.

The surface oxides can be blended in any suitable ratio, such as at a ratio of between about 59.9% (by weight) and about 99.9% eutectic gallium alloy, to about 0.1% (by weight) and about 2.0% gallium oxide. For example percentage by weight of gallium alloy blended with gallium oxide is about 60%, 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater, such as about 99.9% eutectic gallium alloy while the weight percentage of gallium oxide is about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, and about 2.0% gallium oxide. In embodiments, the eutectic gallium alloy can include gallium-indium or gallium-indium-tin in any ratio of the recited elements. For example, a eutectic gallium alloy can include gallium and indium.

The weight percentage of gallium in the gallium-indium alloy can be between about 40% and about 95%, such as about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

Alternatively or in addition, the weight percentage of indium in the gallium-indium alloy can be between about 5% and about 60%, such as about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%.

A eutectic gallium alloy can include gallium, indium, and tin. The weight percentage of tin in the gallium-indium-tin alloy can be between about 0.001% and about 50%, such as about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

The weight percentage of gallium in the gallium-indium-tin alloy can be between about 40% and about 95%, such as about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%.

Alternatively or in addition, the weight percentage of indium in the gallium-indium-tin alloy can be between about 5% and about 60%, such as about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%.

One or more micro-particles or sub-micron scale particles can be blended with the eutectic gallium alloy and gallium oxide. For example, the one or more micro-particles or sub-micron particles can be blended with the mixture with wt % of between about 0.001% and about 40.0% of micro-particles in the composition, for example about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40. In embodiments the particles can be soda glass, silica, borosilicate glass, quartz, oxidized copper, silver coated copper, non-oxidized copper, tungsten, super saturated tin granules, glass, graphite, silver coated copper, such as silver coated copper spheres, and silver coated copper flakes, copper flakes or copper spheres or a combination thereof, or any other material that can be wetted by gallium. In some embodiments the one or more micro-particles or sub-micron scale particles are in the shape of spheroids, rods, tubes, a flakes, plates, cubes, prismatic, pyramidal, cages, and dendrimers. In certain embodiments, the one or more micro-particles or sub-micron scale particles are in the size range of about 0.5 microns to about 60 microns, as about 0.5 microns, about 0.6 microns, about 0.7 microns, about 0.8 microns, about 0.9 microns, about 1 microns, about 1.5 microns, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, about 25 microns, about 26 microns, about 27 microns, about 28 microns, about 29 microns, about 30 microns, about 31 microns, about 32 microns, about 33 microns, about 34 microns, about 35 microns, about 36 microns, about 37 microns, about 38 microns, about 39 microns, about 40 microns, about 41 microns, about 42 microns, about 43 microns, about 44 microns, about 45 microns, about 46 microns, about 47 microns, about 48 microns, about 49 microns, about 50 microns, about 51 microns, about 52 microns, about 53 microns, about 54 microns, about 55 microns, about 56 microns, about 57 microns, about 58 microns, about 59 microns, or about 60 microns.

EXAMPLES

Example 1 is a flexible differential strain sensor, comprising: a deformable substrate having a first axis and a second axis different than the first axis; a first sensing element, comprising conductive gel, arranged to sense strain in the deformable substrate along the first axis; a second sensing element, comprising conductive gel, having a first portion arranged to sense strain in the deformable substrate along the first axis and a second portion arranged to sense strain in the deformable substrate along the second axis; wherein the second sensing element is arranged to cancel at least a portion of the stimulus sensed by the first sensing element in the along the first axis.

In Example 2, the subject matter of Example 1 includes, wherein electrical impedance of the conductive gel of the first and second sensing elements changes in response to a change in strain on the deformable substrate and wherein the first and second sensing elements are configured to sense the strain based, at least in part, on a change in impedance.

In Example 3, the subject matter of Example 2 includes, a signal processing unit, operatively coupled to the first sensing element and to the second sensing element, configured to determine the strain along the first axis by subtracting the change in impedance from the second sensing element from the change in impedance from the first sensing element.

In Example 4, the subject matter of Example 3 includes, wherein the signal processing unit is further configured to determine the strain along the second axis based on the change of impedance from the first sensing element.

In Example 5, the subject matter of Example 4 includes, wherein the signal processing unit is further configured to output a vector indicative of the strain along the first axis and along the second axis.

In Example 6, the subject matter of Example 5 includes, wherein the vector is indicative of a percent change in the strain on the deformable substrate relative to an initial strain.

In Example 7, the subject matter of Example 6 includes, wherein the percent change in strain corresponds to a percent change in deformation of the deformable substrate.

In Example 8, the subject matter of Examples 2-7 includes, wherein the first axis is orthogonal to the second axis and the deformable substrate further has a third axis orthogonal to the first and second axes, and further comprising: a third sensing element, comprising conductive gel, arranged to sense strain in the deformable substrate at least along the third axis.

In Example 9, the subject matter of Examples 1-8 includes, wherein the first sensing portion comprises a first active portion, wherein the second sensing portion includes a second active portion and a cancellation portion, and wherein each of the first active portion, the second active portion, and the cancellation portion includes a variable impedance based, at least in part, on strain placed on the respective first active portion, the second active portion, and the cancellation portion.

In Example 10, the subject matter of Examples 1-9 includes, wherein the deformable substrate is configured to be attached to a structure to determine strain on the structure.

Example 11 is a method of making a flexible differential strain sensor, comprising: obtaining a deformable substrate having a first axis and a second axis different than the first axis; arranging on the deformable substrate a first sensing element, comprising conductive gel, to sense strain in the deformable substrate along the first axis; arranging on the deformable substrate a second sensing element, comprising conductive gel, having a first portion to sense strain in the deformable substrate along the first axis and a second portion arranged to sense strain in the deformable substrate along the second axis; wherein the second sensing element is arranged to cancel at least a portion of the stimulus sensed by the first sensing element in the along the first axis.

In Example 12, the subject matter of Example 11 includes, wherein electrical impedance of the conductive gel of the first and second sensing elements changes in response to a change in strain on the deformable substrate and wherein the first and second sensing elements are configured to sense the strain based, at least in part, on a change in impedance.

In Example 13, the subject matter of Example 12 includes, operatively coupling a signal processing unit to the first sensing element and to the second sensing element, the signal processing unit configured to determine the strain along the first axis by subtracting the change in impedance from the second sensing element from the change in impedance from the first sensing element.

In Example 14, the subject matter of Example 13 includes, wherein the signal processing unit is further configured to determine the strain along the second axis based on the change of impedance from the first sensing element.

In Example 15, the subject matter of Example 14 includes, wherein the signal processing unit is further configured to output a vector indicative of the strain along the first axis and along the second axis.

In Example 16, the subject matter of Example 15 includes, wherein the vector is indicative of a percent change in the strain on the deformable substrate relative to an initial strain.

In Example 17, the subject matter of Example 16 includes, wherein the percent change in strain corresponds to a percent change in deformation of the deformable substrate.

In Example 18, the subject matter of Examples 12-17 includes, wherein the first axis is orthogonal to the second axis and the deformable substrate further has a third axis orthogonal to the first and second axes, and further comprising: arranging on the deformable substrate a third sensing element, comprising conductive gel, to sense strain in the deformable substrate at least along the third axis.

In Example 19, the subject matter of Examples 11-18 includes, wherein the first sensing portion comprises a first active portion, wherein the second sensing portion includes a second active portion and a cancellation portion, and wherein each of the first active portion, the second active portion, and the cancellation portion includes a variable impedance based, at least in part, on strain placed on the respective first active portion, the second active portion, and the cancellation portion.

In Example 20, the subject matter of Examples 11-19 includes, wherein the deformable substrate is configured to be attached to a structure to determine strain on the structure.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to use of any of Examples 1-20.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or any suitable combination thereof), registers; or other machine components that receive, store, transmit, or display information. Furthermore, unless specifically stated otherwise, the terms "a" or "an" are herein used, as is common in patent documents, to include one or more than one instance. Finally, as used herein, the conjunction "or" refers to a non-exclusive "or," unless specifically stated otherwise.

What is claimed is:

1. A flexible differential strain sensor, comprising:
   a deformable substrate having a first axis and a second axis different than the first axis;
   a first sensing element, comprising conductive gel, arranged to sense strain in the deformable substrate along the first axis;
   a second sensing element, comprising conductive gel, having a first portion arranged to sense strain in the deformable substrate along the first axis and a second portion arranged to sense strain in the deformable substrate along the second axis;
   wherein the second sensing element is arranged to cancel at least a portion of the stimulus sensed by the first sensing element in the along the first axis.

2. The flexible differential strain sensor of claim 1, wherein the first sensing portion comprises a first active portion, wherein the second sensing portion includes a second active portion and a cancellation portion, and wherein each of the first active portion, the second active portion, and the cancellation portion includes a variable impedance based, at least in part, on strain placed on the respective first active portion, the second active portion, and the cancellation portion.

3. The flexible differential strain sensor of claim 1, wherein the deformable substrate is configured to be attached to a structure to determine strain on the structure.

4. The flexible differential strain sensor of claim 1, wherein electrical impedance of the conductive gel of the first and second sensing elements changes in response to a change in strain on the deformable substrate and wherein the first and second sensing elements are configured to sense the strain based, at least in part, on a change in impedance.

5. The flexible differential strain sensor of claim 4, wherein the first axis is orthogonal to the second axis and the deformable substrate further has a third axis orthogonal to the first and second axes, and further comprising:
   a third sensing element, comprising conductive gel, arranged to sense strain in the deformable substrate at least along the third axis.

6. The flexible differential strain sensor of claim 4, further comprising a signal processing unit, operatively coupled to the first sensing element and to the second sensing element, configured to determine the strain along the first axis by subtracting the change in impedance from the second sensing element from the change in impedance from the first sensing element.

7. The flexible differential strain sensor of claim 6, wherein the signal processing unit is further configured to determine the strain along the second axis based on the change of impedance from the first sensing element.

8. The flexible differential strain sensor of claim 7, wherein the signal processing unit is further configured to output a vector indicative of the strain along the first axis and along the second axis.

9. The flexible differential strain sensor of claim 8, wherein the vector is indicative of a percent change in the strain on the deformable substrate relative to an initial strain.

10. The flexible differential strain sensor of claim 9, wherein the percent change in strain corresponds to a percent change in deformation of the deformable substrate.

11. A method of making a flexible differential strain sensor, comprising:
    obtaining a deformable substrate having a first axis and a second axis different than the first axis;
    arranging on the deformable substrate a first sensing element, comprising conductive gel, to sense strain in the deformable substrate along the first axis;
    arranging on the deformable substrate a second sensing element, comprising conductive gel, having a first portion to sense strain in the deformable substrate along the first axis and a second portion arranged to sense strain in the deformable substrate along the second axis;

wherein the second sensing element is arranged to cancel at least a portion of the stimulus sensed by the first sensing element in the along the first axis.

12. The method of claim 11, wherein the first sensing portion comprises a first active portion, wherein the second sensing portion includes a second active portion and a cancellation portion, and wherein each of the first active portion, the second active portion, and the cancellation portion includes a variable impedance based, at least in part, on strain placed on the respective first active portion, the second active portion, and the cancellation portion.

13. The method of claim 11, wherein the deformable substrate is configured to be attached to a structure to determine strain on the structure.

14. The method of claim 11, wherein electrical impedance of the conductive gel of the first and second sensing elements changes in response to a change in strain on the deformable substrate and wherein the first and second sensing elements are configured to sense the strain based, at least in part, on a change in impedance.

15. The method of claim 14, wherein the first axis is orthogonal to the second axis and the deformable substrate further has a third axis orthogonal to the first and second axes, and further comprising:

arranging on the deformable substrate a third sensing element, comprising conductive gel, to sense strain in the deformable substrate at least along the third axis.

16. The method of claim 14, further comprising operatively coupling a signal processing unit to the first sensing element and to the second sensing element, the signal processing unit configured to determine the strain along the first axis by subtracting the change in impedance from the second sensing element from the change in impedance from the first sensing element.

17. The method of claim 16, wherein the signal processing unit is further configured to determine the strain along the second axis based on the change of impedance from the first sensing element.

18. The method of claim 17, wherein the signal processing unit is further configured to output a vector indicative of the strain along the first axis and along the second axis.

19. The method of claim 18, wherein the vector is indicative of a percent change in the strain on the deformable substrate relative to an initial strain.

20. The method of claim 19, wherein the percent change in strain corresponds to a percent change in deformation of the deformable substrate.

* * * * *